(12) United States Patent
Kaendler

(10) Patent No.: US 6,458,267 B2
(45) Date of Patent: Oct. 1, 2002

(54) SAMPLE FLUID FILTERING DEVICE

(75) Inventor: Holm Kaendler, Muellheim (DE)

(73) Assignee: Bran + Luebbe GmbH, Norderstedt (DE)

(*) Notice: Subject to any disclaimer, the term of this patent is extended or adjusted under 35 U.S.C. 154(b) by 0 days.

(21) Appl. No.: 09/759,631

(22) Filed: Jan. 12, 2001

(30) Foreign Application Priority Data

Jan. 12, 2000 (DE) ......................................... 100 00 908
Jun. 24, 2000 (DE) ......................................... 100 30 913
Aug. 25, 2000 (EP) ........................................... 00118490

(51) Int. Cl.$^7$ ............................................. G01N 1/14
(52) U.S. Cl. ................... 210/85; 73/863.23; 73/863.24; 73/863.25; 210/195.1; 210/258
(58) Field of Search .................. 73/863.23, 863.24, 73/863.25; 210/85, 195.1, 167, 258, 416.1, 335

(56) References Cited

U.S. PATENT DOCUMENTS

| | | | |
|---|---|---|---|
| 3,625,065 A | | 12/1971 | Thompson |
| 4,018,089 A | | 4/1977 | Dzula et al. |
| 4,197,098 A | * | 4/1980 | Stiehl et al. |
| 4,501,161 A | * | 2/1985 | Endo et al. |
| 5,033,319 A | * | 7/1991 | Ireland |
| 5,625,156 A | | 4/1997 | Serrels et al. |
| 5,828,458 A | * | 10/1998 | Taylor et al. |
| 5,834,657 A | | 11/1998 | Clawson et al. |

FOREIGN PATENT DOCUMENTS

| | | | |
|---|---|---|---|
| AT | 001 571 U1 | | 7/1997 |
| DE | 93 02 641.2 | | 5/1993 |
| DE | 44 30 378 C2 | | 12/1996 |
| DE | 297 18 049 U1 | | 4/1998 |
| EP | 0 430 021 A2 | | 6/1991 |
| GB | 2 116 521 A | | 9/1983 |
| WO | WO-97/19628 | * | 6/1997 |

* cited by examiner

Primary Examiner—Joseph W. Drodge
Assistant Examiner—Terry K. Cecil
(74) Attorney, Agent, or Firm—Michael J. Striker

(57) ABSTRACT

A filter device is described for obtaining a filtered sample of fluid for measuring purposes from a container or tube conduit. The device has a closed fluid circuit including a first filter element 4, a pump conduit having a pump 27 therein, and a second filter element 5 arranged so that a sample of fluid is suctioned from the container or tube conduit via the first filter element 4, through the pump conduit 26, 28 and then back to the container or tube via the second filter element 5 or vice versa. An optical probe 17 for measuring purposes can be arranged within the carrier tube 7.

11 Claims, 1 Drawing Sheet

SAMPLE FLUID FILTERING DEVICE

BACKGROUND OF THE INVENTION

The present invention relates to a filter device for filtration of fluids, in particular with extraction of a filtered sample fluid from containers and tube conduits for measuring purposes.

In known filters of this type the sample fluid is extracted from containers and tube conduits for measuring purposes and after the measurement is rejected. This has the disadvantage that the sample fluid is lost. Further disadvantages of known filter devices resides in that, for cleaning purposes a larger throughput of sample fluid and a greater expense for the sample preparation is required, and the installation cost is high. Other filter devices have the disadvantage of a low filtering rate or of an uncomplete exchange of the sample fluid given a change of the sample fluids. Often a sterile operation is only possible with high apparatus expense.

SUMMARY OF THE INVENTION

Accordingly, it is the object of the invention to provide a filter device with which a sterile handling of the sample fluid is possible with a low cost with regard to an apparatus.

In keeping with these objects, one feature of the present invention resides, briefly stated, in filter device which has a closed fluid circuit including at least one first filter element, a fluid pump, a second filter element arranged so that a sample fluid is suctioned via said first filter element out of a container or tube conduit and via said second filter element is pumped back into the container or tube conduit, or vice versa.

The filter device according to the invention has the advantage that during the measurements no sample fluid is used up, since it is continuously led back again in a closed fluid circuit into the container or the tube conduit from which it was taken. The filter elements keep back dirt particles and in particular bacteria, and thus ensure a sterile sample fluid. Since the closed fluid circuit is provided, the sample fluid also in the further course is not contaminated by the filter system.

In accordance with another feature of the invention the pump direction is reversible. By reversing of the pump direction a cleaning effect may be achieved, since the particles and bacteria filtered out for example by the first filter during the original pump direction and clinging to this first filter, are flushed away with the reversed pump direction and the first filter is thus cleaned. Thereby the servicable duration of the filter device is advantageously increased, in particular when the reversal procedure is repeated at several time intervals.

In accordance with a further inventive feature, the device is further improved in that, the pump direction is automatically reversible, preferably periodically. This construction spares the manual switch-over of the pump and ensures a long trouble-free operation since the switch-over may thus no longer be forgotten.

It is further feature of the invention that the filter elements are exchangeable and thereby the filter fineness and the volume flow through the filter device can be adjusted by exchanging variously designed filter elements. The filter device can be thus advantageously adapted to the various requirements of the measuring operation without great expense.

In a preferred embodiment of the invention, the device elements are mounted on a common assembly carrier. As a result a compact construction of the filter device is provided, which needs only a little sample fluid, is flexible and permits further advantageous design forms.

In a particularly simple, inexpensive and useful embodiment of the invention, the assembly carrier can designed as a carrier tube. A probe flange, a process flange, a first tubular filter element, a separating ring or O-ring, a second tubular filter element and a closure screw screwed into the tube end can be arranged on the carrier tube. This provides the advantage that the components are manufactured with little expense, are easy to keep clean and can be assembled in a simple manner, in the specified sequence. They are simply stuck on the carrier tube and rigidly connected to one another by a closure. Furthermore the tubular formation of the filter elements has the advantage of a relatively large filter surface which permits a large volume throughput.

A further advantage of this construction resides in that the components may be easily exchanged, and specifically not only when a replacement is needed. In particular the filter elements here can be exchanged for other filter elements with other properties, for example with a different filter fineness and a different volume flow, if a greater or lesser throughput of the sample fluid is desired.

The separating ring can be provided for preventing a direct spilling over of a sample fluid from the inflow region into the outflow region. This is achieved by sealing from one another of the two annular spaces arranged radially within the tubular filter elements, and also by sealing the end faces of the filter elements, so that here no fluid can exit. For this purpose the separating ring is designed relatively complex and consists, for example, of a profiled metal ring which is provided with four O-ring seals. If however filter elements are used with a sealing of the end faces due to the construction type, the separating ring can be replaced by a simple O-ring which now only needs to seal the two mentioned annular spaces from one another.

The connection of fluid conduits to the pump and back is simplified in the inventive device, in that the probe flange and the process flange are each provided with a connection bore for the inflow and outflow of sample fluid.

Advantageously a measuring arrangement is integrated within the filter device. This feature uses the fact that the fluid flow within the filter device is accessible without additional expense with regard to apparatus. By way of saving of diversions of the measuring arrangement, the total quantity of circulating sample fluid is advantageously small.

In accordance with the invention, it is recommended for the measuring arrangement to include an optical probe. Therefore, by probes many properties of the sample fluid may be determined without chemically changing it.

The inventive filter device can be narrowed when according to the invention a measuring probe is arranged within the carrier tube. Thus the installation space which is available here can be efficiently used.

The optical probe can have an essentially cylindrical shape, and its free end arranged in the region of the closure screw can be provided with a spacer sleeve. The probe can be centered in the carrier tube and fixed in a defined position, which is particularly advantageous with optical measurements. Therefore, the dead space within the carrier tube and the total circulating fluid quantity can be also reduced.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
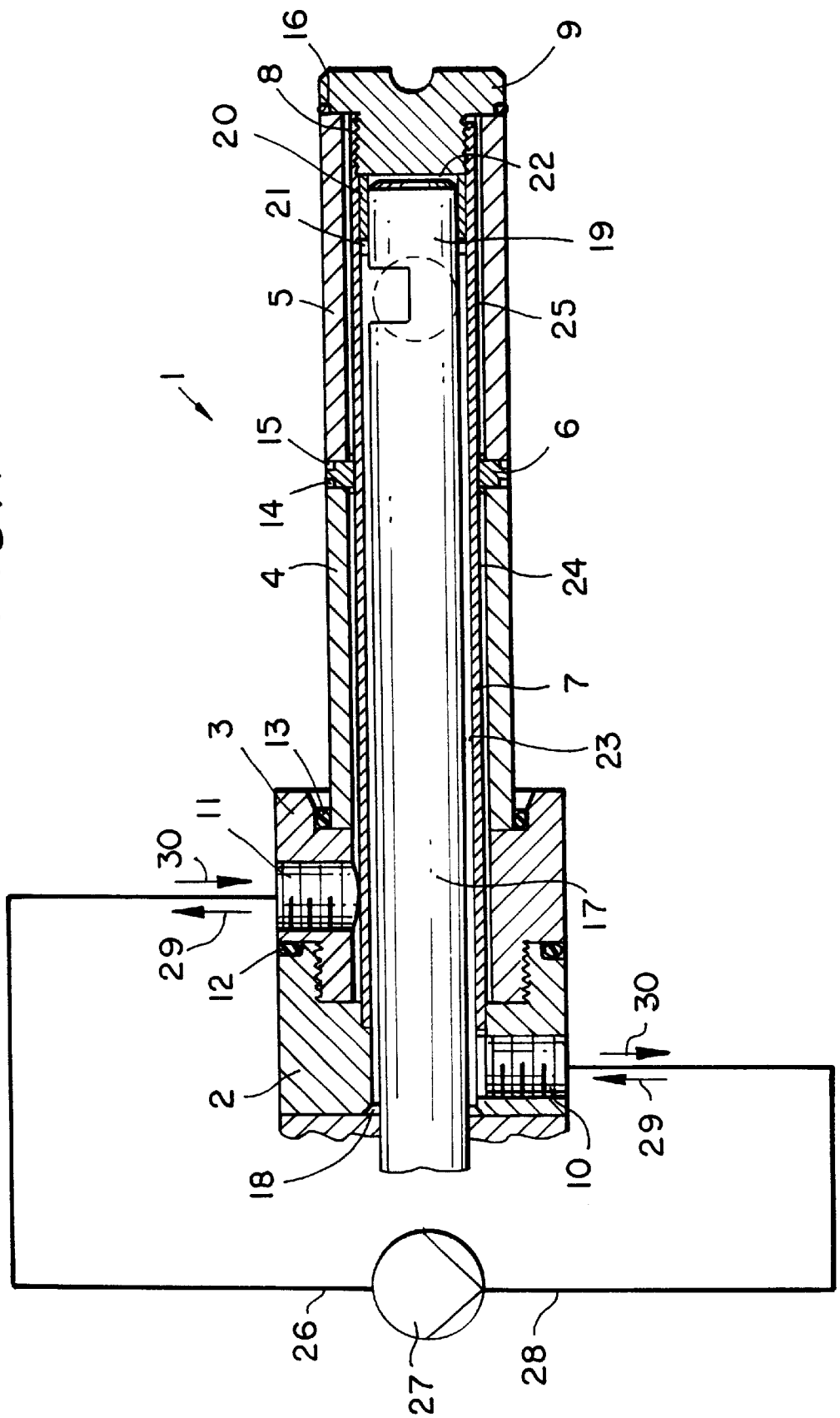
FIG. 1 shows a filter device according to the invention, partly in section, and partly in a schematic representation.

A filter device in accordance with the invention is identified as a whole with reference 1. It has a probe flange 2, a process flange 3, a first tubular filter element 4, a separating ring 6 and a second tubular filter element 5 in the mentioned sequence, which are stuck onto a carrier tube 7 serving as a assembly carrier. A closure screw 9 is screwed into the tube end 8 of the carrier tube 7 and rigidly connects the components to one another. All mentioned components are sealed with respect to one another with sealing rings 12, 13, 14, 15, 16.

In order to assemble the filter device 1, the mentioned components in the mentioned sequence are stuck onto the carrier 7 with the addition of the respective sealing ring, and the closure screw 9 is screwed into the tube end 8. The disassembly of the filter device 1 is performed in the reverse sequence. The filter elements 4, 5 can be exchanged in a simple manner for others with different properties, for example when a different filter fineness or another volume flow is desired.

A measuring arrangement is arranged inside of the carrier tube 7 of the filter device 1. It is formed as an essentially cylindrical optical probe 17 which in the region of the probe flange 2 is sealed by a sealing ring 18. With its free end 19 the probe 17 is inserted into a spacer sleeve 20 which borders on the closure screw 9. The spacer sleeve is arranged within the carrier tube 7 and centered by it. The dead space 22 in the region of the spacer sleeve 20 is sealed by a further sealing ring 21 which borders the spacer sleeve 20, between the carrier tube 7 and the probe 17.

The probe flange 2 is provided with a connection bore 10 for the inflow and outflow of sample fluid. A suitable connection bore 11 is provided in the process flange 3. A first pump conduit 26 is connected with the connection bore 10 of the probe flange 2 and leads to a fluid pump 27. From the fluid pump 27 a second pump conduit 28 leads to the connection bore 11 of the process flange 3. The connection bore 10 of the probe flange 2 opens into an inner annular space 23 which is formed between the probe 17 and the carrier tube 7. The connection bore 11 of the process flange 3 opens into a first outer annular space 24 which is formed between the first filter element 4 and the carrier tube 7. A second outer annular space 25 is formed between the second filter element 5 and the carrier tube 7. The first outer annular space 24 is separated by the separating ring 6 from the second outer annular space 25, so that the sample fluid may not directly spill over.

During the operation the filter device is inserted in a not shown container or tube conduit, so that the two filter elements 4, 5 are surrounded by the fluid to be examined. After the starting operation of the fluid pump 27, it for example pumps the sample fluid in the direction of the arrows 29 so that the fluid to be examined is suctioned through the filter element 4 and is filtered. Solid matter particles and bacteria are, deposited on the outer side of the filter element 4 and do not get into the first outer annular space 24 from where it flows via the connection bore 11 of the process flange 3 and the first pump conduit 26 into the fluid pump 27 and is then pumped further through the second pump conduit 28 via the connection bore 10 of the probe flange 2 into the inner annular space 23. Here the optical measurements of the properties of the sample fluid are performed, until it reaches the second outer annular space 25 and through the second filter element 5 is led radially outwards back into the above mentioned and not shown container or tube conduit. Thus the fluid circuit is closed and no fluid is lost.

After a certain operational time the pump direction of the fluid pump 27 is reversed by a not shown control device, so that the sample fluid from now on moves in the direction of the arrows 30. The fluid is thus suctioned via the second filter element 5 and reaches in the reverse path the first filter element 4, through which the sample fluid flows radially from the inside to the outside. The solid matter particles and bacteria, which with the preceding measuring operation were deposited on the outer side of the first filter element, are rinsed away, so that for the further operation again a clean outer surface is made available.

The above described filter system thereby provides the filtration of fluids with laboratory, process and environmental applications in containers and tube conduits with an integrated measuring arrangement which offers the sterile filtering and the complete exchange of fluid with a closed fluid circuit and simultaneously offers the possibility of varying the filter fineness and volume flow. The inventive filter device can open new fields of application.

It will be understood that each of the elements described above, or two or more together, may also find a useful application in other types of constructions differing from the types described above.

While the invention has been illustrated and described as embodied in filter device, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A filter device for filtration of fluids with extraction of a filtered sample fluid from containers and tube conduits for measuring purposes, the filter device comprising a closed fluid circuit including at least one first filter element, at least one pump conduit having a fluid pump therein, and a second filter element and arranged so that when said first and second filter elements are positioned within a container or tube conduit, a sample fluid is suctioned via said first filter element out of the container or tube conduit and is pumped back via said pump conduit and said second filter element into the container or tube conduit, or vice versa, said filter device further comprising a common assembly carrier formed as a tube, said first and second filter elements being assembled coaxially on a different portion of an outer surface of said tube.

2. A filter device as defined in claim 1, wherein said pump is a direction reversible pump.

3. A filter device as defined in claim 2, wherein said pump is a pump adapted to automatically reverse the flow direction therethrough.

4. A filter device as defined in claim 3, wherein said pump is a pump adapted to periodically automatically reverse the flow direction therethrough.

5. A filter device as defined in claim 1, wherein said filter elements are exchangeable so that filter fineness and volume flow through the filter device are adjustable by exchanging said filter elements with variously designed filter elements.

6. A filter device as defined in claim 1 further comprising a probe flange, a process flange, a separating ring, and a closure screw screwed into an end of said carrier tube, wherein, said probe flange, said process flange, and said separating ring are arranged on said carrier tube.

7. A filter device as defined in claim 6, wherein said probe flange and said process flange are each provided with a connection bore for inflow and outflow of the sample fluid.

8. A filter device as defined in claim 1 further comprising a measuring arrangement integrated in the filter device.

9. A filter device as defined in claim 8, wherein said measuring arrangement includes an optical probe.

10. A filter device as defined in claim 9, wherein said common assembly carrier is provided with a closure screw, and further comprising a spacer sleeve, said optical probe having a substantially cylindrical shape and a free end arranged in a region of said closure screw and provided with said spacer sleeve.

11. A filter device as defined in claim 8, wherein said measuring arrangement is arranged within said carrier tube.

* * * * *